United States Patent
Simi et al.

[11] Patent Number: 5,908,600
[45] Date of Patent: Jun. 1, 1999

[54] MONITOR FOR DETECTING HYDROCARBONS AND OTHER GASES IN AN OPEN AREA

[75] Inventors: Victor M. Simi; Ashok Murthy, both of Lexington, Ky.

[73] Assignee: APL Group International, LLC, Lexington, Ky.

[21] Appl. No.: 08/684,015

[22] Filed: Jul. 23, 1996

[51] Int. Cl.[6] .......................... G01N 27/04; G01N 27/00; G01N 7/00

[52] U.S. Cl. .......................... 422/90; 324/71.5; 73/23.34

[58] Field of Search .......................... 324/71.5; 73/23.34; 422/90

[56] References Cited

U.S. PATENT DOCUMENTS

| | | | |
|---|---|---|---|
| 3,961,248 | 6/1976 | Kawamura | 324/71 SN |
| 4,457,161 | 7/1984 | Iwanaga et al. | 73/23 |
| 4,542,640 | 9/1985 | Clifford | 73/23 |
| 4,638,443 | 1/1987 | Kaneyasu et al. | 364/497 |
| 4,644,333 | 2/1987 | Barendsz et al. | 340/634 |
| 4,818,348 | 4/1989 | Stetter | 204/17 |
| 5,177,994 | 1/1993 | Moriizumi et al. | 73/23.34 |
| 5,223,783 | 6/1993 | Wilis | 324/71.5 |
| 5,321,146 | 6/1994 | Royster et al. | 556/57 |

FOREIGN PATENT DOCUMENTS

| | | |
|---|---|---|
| 2 438 271 | 4/1980 | France . |
| 2 086 583 A | 5/1982 | United Kingdom . |
| WO 93/08467 | 4/1993 | WIPO . |

OTHER PUBLICATIONS

PCT/US97/12740 International Search Report, Nov. 5, 1997.
Patent Abstracts of Japan, JP 03 211415, European Patent Office, Sep. 17, 1991.

*Primary Examiner*—Frank C. Eisenschenk
*Assistant Examiner*—Hankyel T. Park
*Attorney, Agent, or Firm*—Frederick H. Gribbell; James P. Davidson

[57] ABSTRACT

An improved area monitor for detecting gas concentration is provided that requires a very infrequent calibration, and works reliably in detecting a particular target gas using only two semiconductor sensors. One of these sensors will exhibit a drift that is constantly monitored and automatically compensated for, while the other sensor exhibits a stable, repeatable response over very long periods of time. Once the "stable" has been initially calibrated, the concentration of the target gas can be discerned directly from the resistance of this sensor, although more that one particular chemical gas may cause the stable sensor to change resistance. The second sensor is then used to discern whether or not the change in resistance of the stable sensor was due to the actual target chemical, or due to some other similar chemical. The second sensor is selected to be of a type that responds in one direction (i.e., its change in resistance either increases or decreases) when emersed in the particular target chemical of interest. For all other similar gases, the resistance of the second sensor will change in the opposite direction.

20 Claims, 4 Drawing Sheets

MONITOR FOR DETECTING HYDROCARBONS AND OTHER GASES IN AN OPEN AREA

TECHNICAL FIELD

The present invention relates generally to gas-sensing equipment and is particularly directed to a gas sensor of the type which detects a concentration of a particular gas in a relatively open area. The invention is specifically disclosed as an area monitor that can detect the concentration of a particular gas, such as a hydrocarbon, by using only two semiconductor sensors.

BACKGROUND OF THE INVENTION

Gas detecting systems have been available in the prior art in which a plurality of sensors are used, each sensor having a different response characteristic from the other. In U.S. Pat. No. 4,638,443, a gas detecting apparatus is disclosed that determines a ratio of conductivity of each sensor as it becomes exposed to the gas sample. Various mathematical formula are used, including logarithmic operations, to obtain a linear relationship of the conductivity ratio versus the concentration of the particular gas in question. This system then finds "detection patterns," and calculates a "degree of similarity." Once this information has been derived, the gas detecting apparatus can discern the presence of the particular target gas by use of the detection patterns and degree of similarity.

In U.S. Pat. No. 4,542,640 an array of gas sensors is used each having a different response to the selected gases. In this system, at least as many sensors are required as different gases to be detected. The various response patterns of the array of sensors are used to create simultaneous equations, which then can be solved to determine the presence of the selected target gases.

In U.S. Pat. No. 4,457,161, a gas detection system is disclosed in which a sensor array is used to detect concentrations of multiple types of gases. Each sensor has a different sensitivity to the particular target gases, and the sensor's voltage outputs can be quantified by use of simultaneous linear equations.

In U.S. Pat. No. 4,818,348 a system for identifying and quantifying simple and complex chemicals is disclosed. The materials to be analyzed are heated and vaporized. A sensor array is used in which each sensor has a response characteristic that is different from the other sensors. A response pattern is created and compared to a stored pattern to identify the chemical of interest, and this information is independent of concentration. The concentration can then be determined by solving simultaneous equations.

A major problem with conventional chemical analysis systems is that they really do not work well at all. In order to achieve workable simultaneous equations that can be analyzed to find either the presence of a target gas or the concentration of the target gas, the response of the individual sensors in the array of sensors must be very repeatable, and must not drift over time. This is difficult enough to achieve with one or two sensors, and is nearly impossible when using high numbers of sensors (e.g. five or more sensors). Conventional systems that can analyze the presence or concentration of gases in an open area typically use five or more different sensors, in order to have enough information be somewhat reliable in predicting a minimum concentration of important or dangerous gases. The sensors must be calibrated very frequently, or else the calculations used to make the determination of the presence of a particular gas will become quite useless.

It would be desirable to provide a gas detecting system that did not require recalibration at very short time intervals. In addition, it would be desirable for such a system to use relatively few sensors, regardless of whether or not such sensors exhibit severe drift problems (whether such sensors are repeatable or stable over long periods of time). It would be even more desirable to correct for drift of sensors that are not repeatable or stable over long periods of time.

SUMMARY OF THE INVENTION

Accordingly, it is a primary object of the present invention to provide a gas detecting system, usable in an open area for detecting the presence of one or more target gases, which requires only a very infrequent calibration.

It is another object of the present invention to provide a gas detecting system to monitor open areas that uses very few sensors, including as little as two sensors in reliably detecting the presence and/or concentration of a particular target gas.

It is a further object of the present invention to provide a gas detecting system for monitoring open areas that automatically corrects for drift in at least one of the sensors used in detecting one or more target gases.

Additional objects, advantages and other novel features of the invention will be set forth in part in the description that follows and in part will become apparent to those skilled in the art upon examination of the following or may be learned with the practice of the invention.

To achieve the foregoing and other objects, and in accordance with one aspect of the present invention, an improved area monitor for detecting gas concentration is provided that requires a very infrequent calibration, and works reliably in detecting a particular target gas using only two sensors. These sensors preferably are semiconductor sensors, and one sensor will exhibit a drift that is constantly monitored and automatically corrected for. The other sensor preferably exhibits a response that is repeatable to the extent that it is stable over very long periods of time, for example, as much as one year.

Each of the two sensors is connected into a buffer amplifier that outputs a usable analog voltage into a multi-channel multiplexer. The analog voltage of each sensor is, one at a time, then introduced to an analog-to-digital converter, and this information is presented to a computer device, such as a microprocessor. The output voltage from the stable sensor is determined, and from that information the resistance of the sensor in kilo-ohms ($K\Omega$) is calculated. Once this sensor has been initially calibrated, the concentration of the target gas can be discerned directly from the resistance of this sensor. However, more that one particular chemical gas may cause the stable sensor to change resistance, and the second sensor of the system is then used to discern whether or not the change in resistance of the first sensor was due to the actual target chemical, or due to some other similar chemical (probably from the same chemical family).

From the output voltage of the second sensor, its resistance in $K\Omega$ is calculated. The second sensor is selected to be of a type that responds in one direction (i.e., its change in resistance either increases or decreases) when emersed in the particular target chemical of interest. For all other similar gases, the resistance of the second sensor will change in the opposite direction. When this information is combined with the resistance reading from the first sensor, it can be determined whether or not the monitoring system has detected the presence of a particular target gas, and if so, the concentration of the target gas is then known.

In the illustrated embodiment, the second sensor is not a highly stable sensor, since it exhibits a relatively large drift over short time intervals. However, this drift can be compensated for once an initial value of the resistance for the second sensor is known under the condition where the second sensor is immersed in an area that does not contain the target gas of interest. Once this initial value of the second sensor's resistance is known, its resistance can be periodically measured at time intervals while the first sensor periodically samples the same area. If the resistance of the second sensor begins to drift, and if the first sensor is not detecting a concentration of the target gas above a certain threshold (e.g., "a minimum" threshold below which the area monitor does not concern itself with concentration of the target gas), then the "new" resistance value of the second sensor (caused by its drift) can be stored in the microprocessor's memory system. This latest value of the second sensor's resistance can be used, for all practical purposes, as the latest calibration value of the resistance of the second sensor in a gas concentration that does not contain the target gas. This updated value for the resistance of the second sensor can change quite slowly, but by a significant extent, and these re-calibrations do not affect the operation of the overall area monitor system so long as the first sensor does not detect the minimum threshold concentration of the target gas. If the sampling occurs quickly enough (e.g., once per second), then the area monitor system essentially re-calibrates the resistance value of the second sensor at every periodic scan of the outputs of both sensors.

Once the first sensor exhibits an output that indicates the concentration of the target gas has increased above the minimum threshold of interest, then the resistance of the second sensor is compared to its most recent "drift-corrected" value, and this comparison will provide the indication as to whether or not the change in resistance of the first sensor is due to the target gas, or it is due to some other similar gas that is not the target gas. In this manner, a very accurate system for detecting the concentration of a particular target gas is provided, and is dependant only upon relatively long-interval calibrations of the first sensor's output characteristics. In the illustrated embodiment, the first sensor is sufficiently stable so as to require calibration only once per year. This relatively infrequent re-calibration is a very significant improvement over conventional gas detecting systems.

Using the power of the multiplexed inputs and the microprocessor, the present invention can monitor several zones of pairs of sensors virtually simultaneously, and can detect gas concentrations in those several areas in real time. If the first sensor of a particular zone exhibits a change in resistance indicating that the concentration of the target gas has exceeded the minimum threshold, then the second sensor is immediately inspected to determine whether or not the change in resistance of the first sensor was truly due to the target gas or not. If the answer is YES, then the concentration (based upon the resistance value of the first sensor) is inspected to determine whether or not an alarm should be energized, particularly in situations where the target gas is dangerous in some respect (e.g., the target gas may be explosive).

In the illustrated embodiment, both sensors are repeatedly inspected (or "sampled") once per second, and their resistance values are placed into a data table residing in the memory associated with the microprocessor. If the concentration of the gas, as indicated by the first sensor, falls below the minimum threshold value, then the data table is loaded with the value of zero for two different data tables: (1) a "target gas buffer" and (2) an "other gas buffer." In addition, a third data table or buffer is loaded with the latest value for the resistance of the second sensor.

Once the first sensor's resistance changes such that the concentration of the target appears to exceed the minimum threshold value, then, depending upon the determination provided by the second sensor's resistance, either the "target gas" data table will begin to be loaded with values other than zero, or the "other gas" data table with begin to be loaded with values other than zero. In the circumstances where the value of the second sensor indicates that the target gas is present in the area, then the "target gas" data table is loaded with a new value after each scan (i.e., after each one-second periodic interval). The system user preferably will have entered a setpoint that will be used for the minimum concentration of the target gas that will be considered as an alarm condition. If the "target gas" data table is loaded with values having an average that exceeds the minimum threshold but do not exceed the alarm setpoint, then the video display associated with the microprocessor system will preferably indicate a change in the status by changing the numerical value of the gas concentration on the video display. If the "target gas" buffer becomes loaded with concentration values having an average that exceeds both the minimum threshold and the user-entered alarm setpoint, then the video display preferably should change a color indicator from green (i.e., "Normal") to red, and an audible alarm will also preferably become energized.

If the resistance value of the second sensor indicated that it is not the target gas being sensed by the first sensor, then the "other gas" data table will begin loading with concentration values provided by the first sensor. This information can be numerically displayed on the video display, however, the alarm indicators preferably would not show a condition red or sound an audible alarm regardless of the value of the concentration being displayed. This aspect of the present invention could easily be changed to allow an alarm condition to be indicated, but that would typically not be desirable except in very unusual circumstances. Generally speaking, if the target gas is not being detected, the identity of the gas that is causing the first sensor's resistance to change generally will not be known with enough specificity so as to be sufficiently determinative of any type of alarm condition. However, it is preferred that the color indicator be changed from green to yellow once the minimum threshold is exceeded for an unknown gas.

The time interval over which samples are collected before an alarm is sounded are, in the illustrated embodiment, over a sixty second interval, a fifteen minute interval and an eight hour interval. Of course, different time intervals could be used without departing from the principles of the present invention.

Still other objects of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

Figure 1:
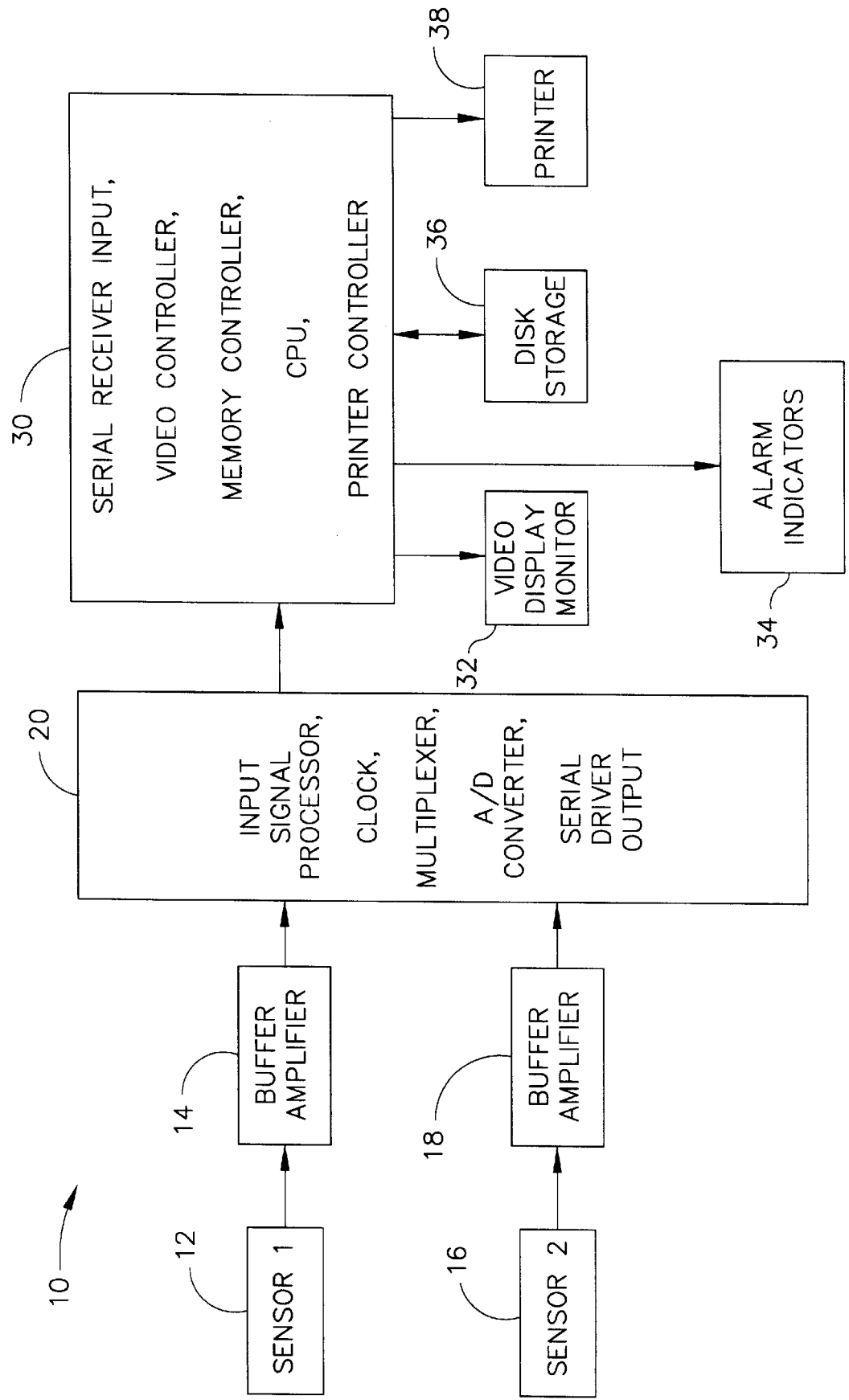
FIG. 1 is a block diagram of the major components of an "area" monitoring system, constructed according to the principles of the present invention.

Referring now to the drawings, FIG. 1 shows a block diagram of the major components used in the area monitor, generally designated by the index numeral 10, of the present invention. Area monitor 10 contains two sensors, at index numerals 12 and 16, each having an individual buffer amplifier, at index numerals 14 and 18, respectively. The outputs of buffer amplifiers 14 and 18 are directed into an input signal processing circuit, which is a portion of the interface electronics designated by the index numeral 20.

The interface circuitry 20 receives the two analog input signals from the buffer amplifiers 14 and 18 and, after data manipulation, also contains a serial output driver that directs digital signals into a microprocessor module 30. Interface circuit 20 includes a 1200 baud clock that not only provides clocking signals for the serial output driver, but also provides clocking signals for a timing generator circuit and input multiplexer. In a preferred embodiment, interface circuit 20 could receive signals from several zones of sensors and buffer amplifiers and, for example, if there were nine zones, there would be eighteen individual analog input signals provided from eighteen individual sensor/buffer amplifier combinations.

A single eighteen-channel multiplexer is used to switch between only one of these analog input signals per particular time interval. The output of the multiplexer is connected to an analog-to-digital (A/D) convertor, which transmits its parallel digital output to a shift register circuit that converts the parallel signal to a serial digital signal. This serial digital signal preferably is sent to an output driver circuit, such as an RS-232 driver circuit, which transmits digital signals to the microprocessor module 30.

As will be described hereinbelow, the interface circuitry 20 also includes a 1.0 Hertz clock that determines the beginning of time intervals during which all of the input channels are multiplexed, converted from analog-to-digital signals, then converted into serial data signals and sent to the microprocessor module 30. It will be understood that many other types of circuitry could be used to interface with multiple analog input signals received from buffer amplifiers 14 and 18 and transmitted into a microprocessor circuit, without departing from the principles of the present invention.

The microprocessor module 30 preferably includes a video controller that communicates to a video display monitor 32, a memory controller that communicates with a disk storage device 36, and a printer controller that communicates with a printer 38. In addition, the computer module 30 preferable controls several digital outputs that can be used as alarm indicators, generally designed by the index numeral 34.

Figure 2:
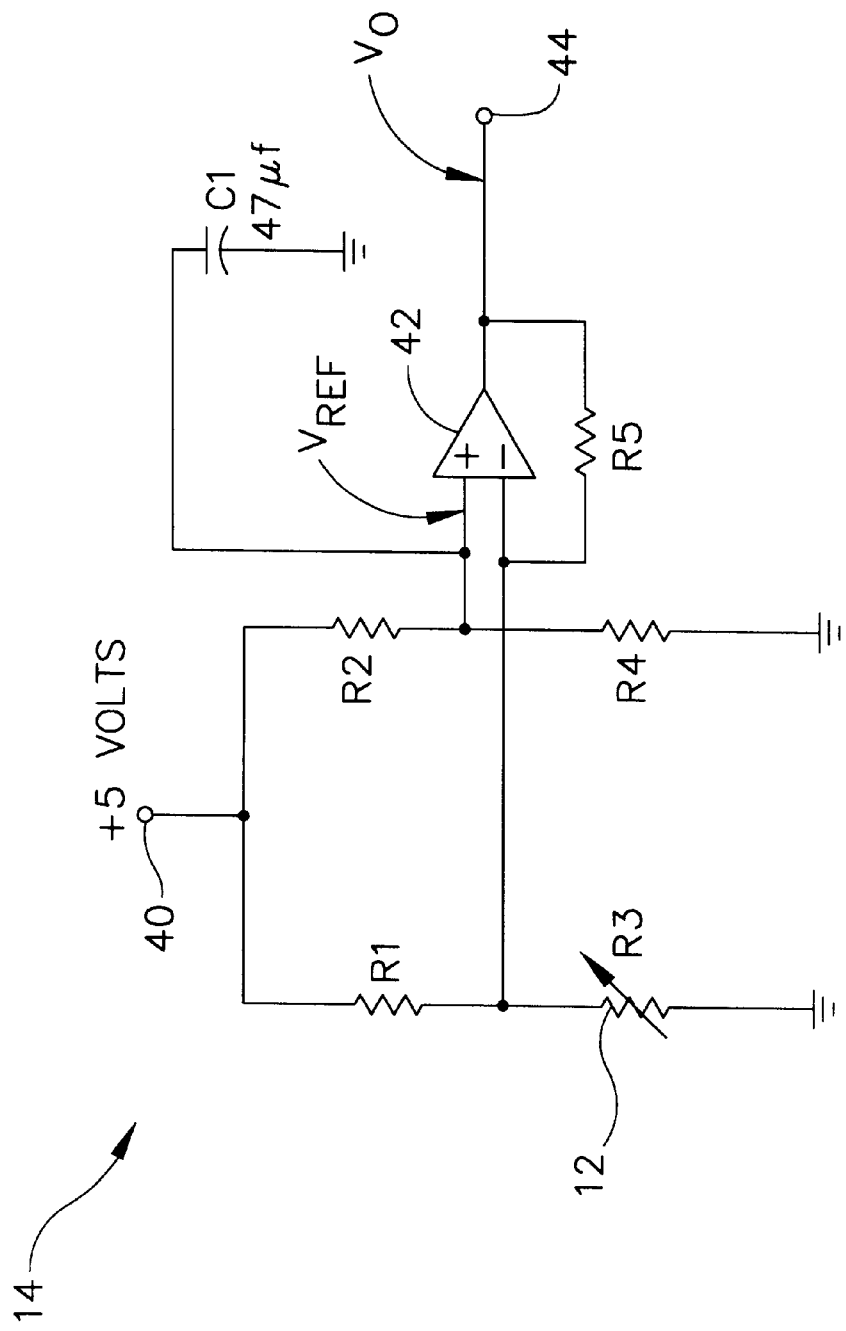
FIG. 2 is a schematic diagram of a buffer amplifier as it is interfaced to one of the gas sensors, as used in the area monitor of FIG. 1.

Sensors 12 and 16 preferably are made of a semiconductive material, in which are commonly available with a tin oxide sensing element. Such semiconductor sensors are available from various manufacturers, and are commonly used in detecting various types of gases throughout the industry. A typical such sensor will effectively change its resistance in the presence of a particular gas that the sensor responds to. This change in resistance can be detected by a proper buffer amplifier circuit, such as provided in buffer amplifiers 14 and 18. FIG. 2 depicts a preferred buffer amplifier circuit used for buffer amplifier 14. An operational amplifier 42 is the primary amplifying means, and its inputs are connected to a resistance network that includes a variable resistance comprising sensor 12.

It will be understood that sensors other than resistance-varying types can be used to provide signals that can be interfaced with an amplifier circuit without departing from the principles of the present invention. For example, sensors that change either current or voltage (rather than changing resistance) could be used with the proper interface circuit to provide signals that can be interpreted by the overall system. Other types of sensors that could be used includes types such as electrochemical, infrared, or accoustic wave, all of which are commercially available.

In FIG. 2, sensor 12 is designated as R3, which is connected between the negative input of op-amp 42 and ground. Resistors R1, R2, R4, and R5, are fixed resistances. The combination of R2 and R4 provides a reference voltage ($V_{REF}$) at the positive input of op-amp 42. A capacitor C1 is preferably connected at this positive input to act as a filter and bypass capacitor. A +5 volt DC power supply is located at the index numeral 40 and the output of buffer amplifier 14 is designated at the index numeral 44. The output voltage of this interface or buffer amplifier is designated $V_0$.

The types of gases that can be detected by the present invention are many, including several types of hydrocarbons. Some of these gases may be explosive, so it could be very important that the sensor and/or its buffer amplifier be housed in an explosion proof enclosure. A list of some of the target gases that can be detected by the present invention follows below:

| | |
|---|---|
| Aliphatics | Methane |
| | Ethane |
| | Decane |
| | Propane |
| Aromatic | Benzene |
| | Naphthalene |
| | Phenols |
| | Toluene |
| Alcohols | Methanol |
| | Ethanol |
| | n-Propanol |
| | Isopropanol |
| | Butenol |
| Aldehydes | Formaldehyde |
| | Glutaraldehyde |
| Ketones | Acetone |
| Carboxylic Acids | Acetic Acid |
| Ethers | Dimethyl Ether |
| Epoxides | Ethylene Oxide |
| | Propylene Oxide |

| | |
|---|---|
| HaloCarbons | Freons |
| Hydrogen Peroxide | |
| Hydrogen | |

An example of sensors that will detect hydrocarbons such as Ethylene Oxide are: for sensor 12, Figaro part number TSG832, and for sensor 16, Figaro part number TSG821. Other specific sensors, made by either Figaro or other manufacturers, can be used to advantage to detect others of the hydrocarbons or other example gases listed in the above table.

The alarm indicators 34 can, for example, consist of an individual indicator lamp for each zone of sensors, and the lamp could indicate an alarm state in which a potentially dangerous concentration of an explosive gas exists. In addition, the alarm indicators 34 could include an audible alarm, such as a horn or a sonalert, or other solid state audio output device (such as a piezo-electric device). Furthermore, the video display monitor 32 can easily depict alarm conditions by changing colors on its screen, in which green could indicate normal and red could indicate danger.

Figure 3:
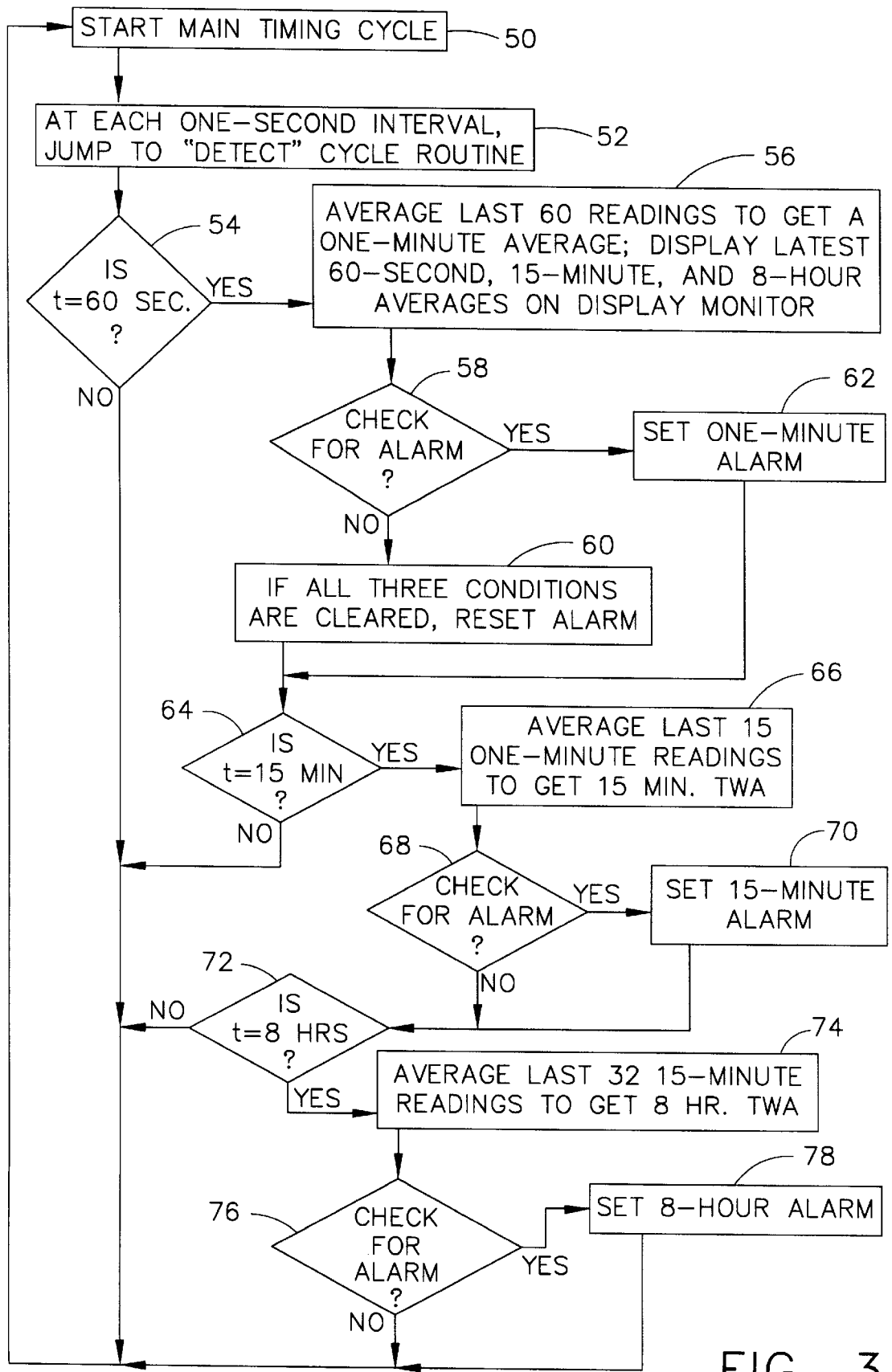
FIG. 3 is a flow chart of the "main timing cycle" used in analyzing whether or not an alarm condition exists in the area monitor of FIG. 1.

FIG. 3 depicts a flow chart of the "main timing cycle" of a computer program that preferably will control the processing of the analog inputs provided by buffer amplifiers 14 and 18, and will also control the displays and alarm indicators at the video monitor 32 and alarm indicators 34. The main timing cycle starts at a function block 50, and continues to a function block 52 that jumps, at the end of each one-second time interval, to a routine or sub-program that detects the analog input values from buffer amplifiers 14 and 18. The steps of this "detect cycle" routine are provided on FIG. 4, and are discussed in greater detail hereinbelow.

Once the program logic returns from the "detect" cycle routine, certain values will have been determined and set into memory locations accessible by the microprocessor. Such values will preferably include the concentration of the target gas (i.e., the gas of interest being detected by the two sensors 12 and 16 in this particular zone). Other such values that are instantaneously available include the resistance (in kΩ) of sensors 12 and 16, designated as $R_A$ and $R_B$, respectively, on FIG. 4. It is preferred that a table of memory buffers be reserved to store previous readings of the concentration of the gas, especially when the target gas has been detected. These memory buffers will be used to create and maintain averages over time of these concentration readings, and preferably will include a sixty-second average, a fifteen-minute average, and an eight-hour average.

After each "detect" cycle routine has been completed (at one-second intervals), the logic flow is directed to a decision block 54 which determines whether or not sixty (60) seconds has elapsed since the previous time that decision block 54 has provided a YES answer. If the answer is NO, then the logic flow returns to the start main timing cycle at function block 50.

If the answer at decision block 54 is YES, then the logic flow is directed to a function block 56 that averages the most recent sixty (60) readings to obtain a one-minute average of the gas concentration. After this occurs, function block 56 will cause the video monitor (global) 32 to display the latest sixty-second average, the latest fifteen-minute average, and the latest eight-hour average on its screen. As related above, the one-minute average is obtained from a data table or buffer in the memory circuitry associated with the computer module 30, in which the most recent sixty (60) values of concentration (as determined by the one-second "detect" cycle program) are stored. As will be understood, this data table preferably comprises sixty separate memory locations in which each memory location is of sufficient size to store enough numerical data to represent a value of concentration of the target gas. Such a memory location may consist of several bytes of physical memory space especially where floating point numbers are used. A one-minute average can be represented as an arithmetic mean, or it can be time-weighted, if desired. The same is true with the fifteen-minute average and the eight-hour average, which preferably are "time-weighted averages."

Once the three different averages have been displayed on the video monitor's screen, the logic flow now checks, at a decision block 58, to see if an alarm condition exists. As related above, it is preferred that a minimum "threshold" detection limit be used to sense whether or not a sufficient concentration of the target gas has become exposed to the sensor array in the zone of interest, at least to the extend that any action should occur other than loading values of zero into the data tables for the various sixty-second, fifteen-minute or eight-hour averages. In addition, it is preferred that the user of the system have the capability of entering an alarm setpoint, which would represent a value of concentration of the target gas which, if exceeded by actual gas concentration, would cause an alarm condition to exist.

Figure 4:
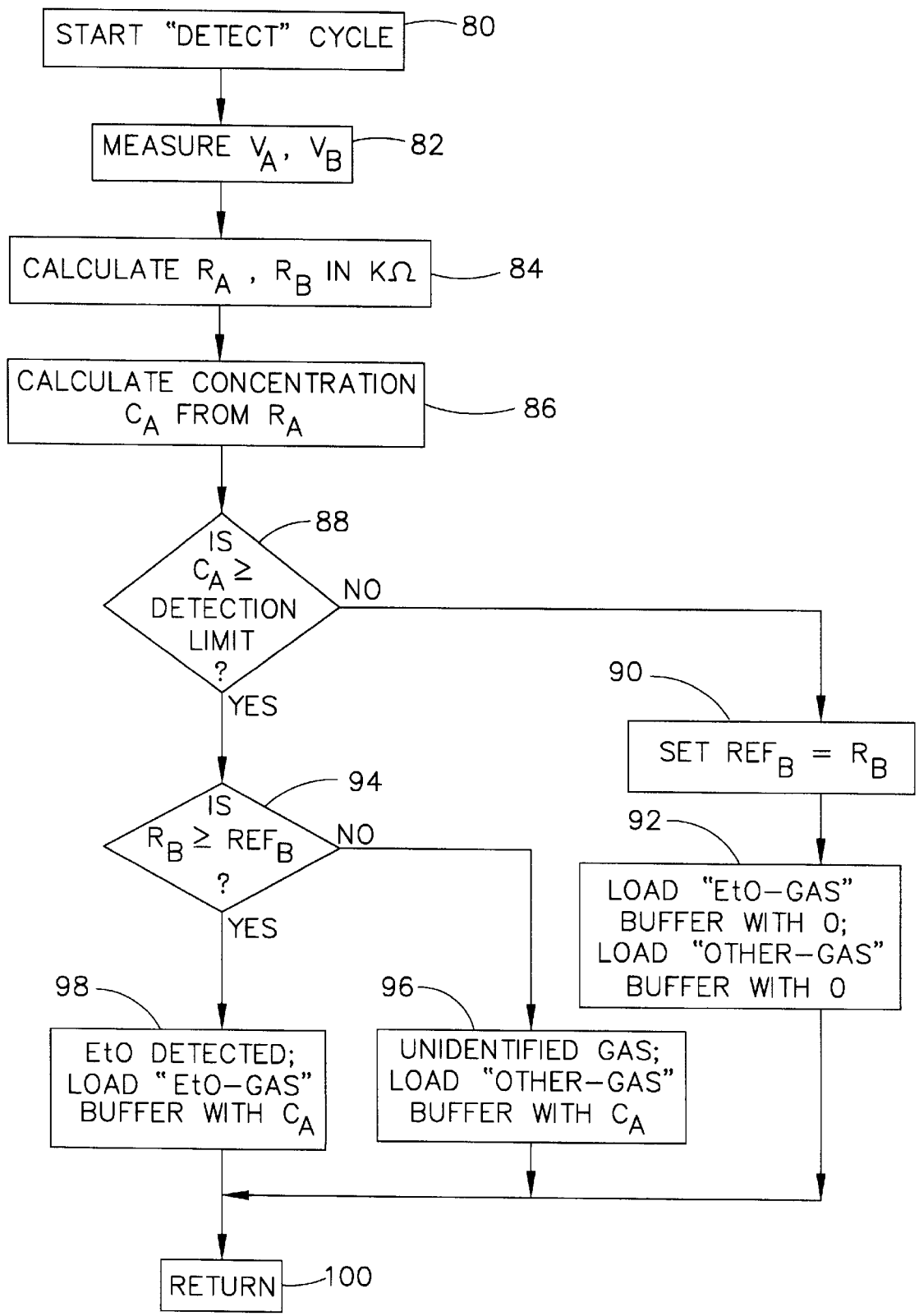
FIG. 4 is a flow chart of the "detect cycle" routine, which is used as one of the functional steps in the flow chart of FIG. 3.

As will be seen in the description of FIG. 4, a minimum threshold limit is used before new calculations other than zero are performed by the computer system 30. However, the test for an alarm condition in function block 58 is preferably related only to the user-entered alarm setpoint condition, which if exceeded, will direct the logic flow out the YES output from decision block 58 to a function block 62 that "sets" the one-minute alarm. Function block 62 is described as setting only the "one-minute alarm" as compared to setting either the fifteen-minute alarm or the eight-hour alarm. Each of these alarm conditions is preferably separated as an independent condition or variable in the computer system 30.

If the answer at decision block 58 was NO, then the logic flow travels to a function block 60, which resets the alarm state if all of the three alarm conditions (i.e., the one-minute, fifteen-minute, and eight-hour alarms) are cleared. The logic flow now travels to a decision block 64, whether the logic flow originated from function block 60 or function block 62.

Decision block 64 determines whether or not fifteen (15) minutes has elapsed since the last time function block 64 provided a YES result. If the answer is NO the logic flow returns to the start main timing cycle at function block 50. If the answer is YES the logic flow is directed to a function block 66 that averages the last fifteen (15) one-minute readings to obtain a fifteen-minute time weighted average. As related above, this average does not necessarily have to be a time weighted average, but could be some other arithmetic value, such as a mean.

After this has occurred, a decision block 68 checks to see if an alarm condition exists for the fifteen-minute average. It is preferred that the fifteen-minute average be obtained from previous one-minute readings, however, it will be understood that other readings could be used instead, such as storing greater amounts of one-second readings to obtain a fifteen-minutes average that is based upon greater numbers of data values.

The alarm condition at decision block 68 preferably is related to the user-entered alarm setpoint (rather that the "minimum threshold" value), and if such an alarm condition exists, the logic flow is directed to a function block 70 that "sets" the fifteen-minute alarm. It will be understood that the concentration value for the fifteen-minute alarm setpoint could be different than the concentration value for the one-minute alarm setpoint, and correspondingly, could be different than the value for the concentration alarm setpoint for the eight-hour alarm.

The logic flow is now directed from either decision block 68 or function block 70 to another decision block 72, where it is determined whether or not eight (8) hours have elapsed since the last time decision block 72 provided a YES result. If the answer is NO, the logic flow is directed back to the start main timing cycle at function block 50. If the answer is YES, the logic flow is directed to a function block 74 that averages the last thirty-two (32) fifteen-minute readings to obtain the eight-hour average. As with the calculations for the one-minute average and fifteen-minute average, the eight-hour average can be an arithmetic mean, however, it is preferably a time-weighted average. Furthermore, it will be understood that other time-related readings could be used and the most recent thirty-two (32) fifteen-minute readings to obtain the eight-hour average.

The logic flow is now directed to a decision block 76 which checks for an alarm condition. This alarm condition preferably will be related to a user-entered eight-hour alarm setpoint, which can be independently adjusted with respect to other alarm setpoints in the system. If no alarm condition is found by decision block 76, the logic flow is directed back to function block 50, where the main timing cycle starts. If decision block 76 detects an alarm condition, the logic flow is directed to a function block 78 that sets the eight-hour alarm. The logic flow now returns to the start main timing cycle at function block 50.

It is preferred that, in all cases of an alarm condition being present, that the video monitor 32 provide an easily seen color indicator that, under normal conditions, would show the color green, and under alarm conditions would show the color red. This color "bar" indicator could be positioned on the monitor's screen at a location very close to the numerical data related to a particular zone of sensors. Preferably, each zone of sensors would have its own color indicator, and also it own numerical indicators for the values being calculated by the system, i.e., the one-minute, fifteen-minute, and eight-hour averages of the concentration of the target gas. In addition, the concentration of an unknown gas (if detected by the system, as described below) can also be numerically indicated on the video monitor 32.

Separate alarm indicators are preferably provided in a separate panel or enclosure, as indicated by index numeral 34 on FIG. 1. The indicator lamp for a particular zone would preferably become illuminated upon the occurrence of any one or more of the alarm conditions described above, and furthermore, an audible alarm would preferably be sounded in situations under which an alarm condition exists. An audible alarm device also could be mounted on the panel or separate enclosure 34.

FIG. 4 is a flow chart that shows the one-second "detect cycle", which begins at a function block 80. This start of cycle would preferably be initiated by the one-second clock that is a portion of the interface module 20 on FIG. 1. All measurements and calculations for all sensors in the system (for all zones) typically would be completed within each one-second interval by a sufficiently powerful computer system. This electronic and mathematical set of functions should pose no problem for conventional personal computer-type microprocessor systems, or other types of data acquisition microprocessor systems which should all have sufficient power to accomplish all of these tasks in less than one second.

The logic flow is directed to a function block 82, which "measures" the voltage levels of sensors 12 and 16. Of course, the voltages provided by sensors 12 and 16 are actually produced by buffer amplifiers 14 and 18, and on FIG. 4, these voltage levels are indicated as the variable $V_A$ for the output of buffer amplifier 14 and $V_B$ for the output of buffer amplifier 18.

The logic flow now is directed to a function block 84 which calculates the actual resistance of sensors 12 and 16 from the voltage values $V_A$ and $V_B$. These resistances are indicated on FIG. 4 as the variables $R_A$ (which relates to $V_A$), and $R_B$ (which relates to $V_B$), and preferably are calculated in engineering units of k$\Omega$. Using the circuit illustrated in FIG. 2, the preferred calculations for $R_A$ and $R_B$ take the form of:

$$R3 = \frac{Vref\ R5}{Vo - Vref + Vref\ R5/R1\ (1-5v)}$$

$$Vref = \frac{5v\ R4}{R2+R4}$$

The logic flow now arrives at a function block 86, which calculates the concentration, (given the variable name $C_A$), from the value of $R_A$. As related above, it is unknown at this point in the "detect" cycle as to whether this concentration $C_A$ represents the concentration of a target gas or of an unknown gas. The value for $C_A$ is calculated from an equation of the form $C_A = X\ (R_A)^Y$, where X and Y are constants determined during the calibration of sensor 12.

The logic flow is now directed to a decision block 88 that determines whether or not the concentration $C_A$ is greater than or equal to the "minimum" detection limit. This minimum detection limit would typically be set by the manufacturer of the area monitor, preferably by software code that cannot be changed by the user. As an example, when detecting ethylene oxide, this minimum detection limit preferably would be set to the value two parts per million (2 ppm). If the answer is NO, then the logic flow is directed to a function block 90 where the "reference" value for the resistance $R_B$ (given the variable name "$REF_B$") is set equal to the current resistance value $R_B$, as determined during this particular detect cycle. This step is critical to compensating for the drift of sensor 16, because it allows sensor 16 to essentially drift all over the map during time periods where the concentration $C_A$ of the target gas is so low as to be essentially undetectable, thereby automatically compensating for this drift by using the most recent value of $R_B$ as determined at function block 84. Function block 90 essentially re-calibrates the resistance $R_B$ of sensor 16 every second (assuming that the "detect cycle" occurs once per second).

The logic flow is now directed to a function block 92 that loads the target gas data table (described as the "EtO-GAS" buffer) with the value zero for this most recent detect cycle. In addition, function block 92 also loads the "OTHER-GAS" buffer with the value for zero for this most recent detect cycle. After this has been accomplished, the logic flow is directed to a function block 100, which returns back to the main timing cycle.

If the answer at decision block 88 was YES, the logic flow is directed to a decision block 94 which determines whether or not the current value of $R_B$ is greater than or equal to the previously established "reference" value $REF_B$. If the answer is YES then the target gas has been detected, as indicated in a function block 98 as "EtO" detected on FIG. 4. Function block 98 then loads the "EtO-GAS" buffer with the most recent value of $C_A$ (as calculated at function block 86). After that has occurred, the logic flow is directed to the return from the subprogram at function block 100.

If the answer at decision block was NO, the logic flow is directed to a function block 96 which stands for the prospect that an unidentified gas has been detected. Function block 96 then load the "OTHER-GAS" buffer with the latest value of $C_A$, as calculated at function block 86. The logic flow then returns to the main timing cycle, via function block 100.

As related above, the resistance of the second sensor (i.e., sensor 16) is a direct indicator as to whether or not the target gas has been detected, as opposed to some unidentified gas that may be introduced into the area being monitored. In the exemplary flow chart of FIG. 4, if the target gas (in this case ethylene oxide or EtO) has been detected, then the value of $R_B$ would have increased as compared to its most recently calculated value for $R_B$, i.e. from its previous "detect cycle". Such a determination directly leads to the conclusion that the target gas was detected, and that function block 98 should now load the value of $C_A$ into the "target gas" buffer, instead of the "other-gas" buffer. In the example of FIG. 4 the target gas buffer is designated the "EtO-GAS" buffer.

Since the value $R_B$ is essentially re-calibrated at every one-second scanning interval, one can be assured that the sudden increase in value of $R_B$ as detected by decision block 94 is truly due to an increase in concentration of the target gas, since the target gas's concentration $C_A$ was essentially minimal or non-existent at the previous one-second scan (as detected by the "detect" cycle of the present invention). When the concentration $C_A$ suddenly exceeds the minimum detection limit, the "reference" value for $R_B$ (i.e., the variable $REF_B$) is essentially "frozen" at its most recently re-calibrated value, and that frozen value is used in the calculation at decision block 94.

Of course, if the value for $R_B$ decreases rather than increasing, then decision block 94 will provide the result that an unidentified gas has been detected. As related above, once this occurs, the "OTHER-GAS" buffer begins being loaded with values of $C_A$, and preferably, the video monitor 32 will indicate a yellow color indicator for this particular zone. This will not raise an alarm condition, however, the color change of the indicator should be sufficient to get the attention of the human user that is monitoring the system.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

We claim:

1. An area monitor for detecting a gaseous compound, comprising:

(a) a first sensor that exhibits a physical parameter that responds to variations in concentration of a pre-determined target gas within an area of detection, said first sensor's physical parameter being substantially repeatable at various concentrations of said target gas, said first sensor's physical parameter being substantially stable over long periods of time;

(b) a second sensor that exhibits a physical parameter that responds to variations in concentration of said pre-determined target gas within said area of detection, said second sensor's physical parameter changing in one direction when in the presence of said target gas, said second sensor's physical parameter changing in the opposite direction when in the presence of a gas other than the target gas that becomes introduced into said area of detection; and (c) a monitoring system that interfaces with said first and second sensors, said monitoring system detecting the physical parameter of said first sensor and creating an output signal that varies with respect to the concentration of said target gas, said monitoring system having a clock circuit that, at pre-determined time intervals, repeatedly detects the physical parameter of said second sensor and, if the concentration of the target gas as determined by the physical parameter of said first sensor is below a pre-determined threshold value, re-calibrates said second sensor at each pre-determined time interval, thereby automatically compensating for any drift over time in the physical parameter value of said second sensor.

2. The area monitor as recited in claim 1, wherein said physical parameter comprises an electrical resistance.

3. The area monitor as recited in claim 2, wherein said monitoring system further detects whether the concentration of the target gas as determined by the resistance of said first sensor has exceeded a pre-determined alarm setpoint, and, if the resistance of said second sensor indicates that said target gas is present in the area of detection, said monitoring system initiates an alarm condition.

4. The area monitor as recited in claim 3, wherein said monitoring system, as part of the initiation of an alarm condition, sounds an audible alarm and illuminates a red indicator.

5. The area monitor as recited in claim 3, further comprising a "target gas data table" as part of a memory circuit, and wherein numeric values of the concentration of the target gas, as determined by the resistance of said first sensor, are stored into said "target gas data table" during an alarm condition.

6. The area monitor as recited in claim 2, wherein in circumstances where said monitoring system detects whether the concentration of the target gas as determined by the resistance of said first sensor has exceeded said pre-determined threshold value, and if the resistance of said second sensor indicates that said target gas is not present in the area of detection, said monitoring system initiates an "other-gas detected" condition.

7. The area monitor as recited in claim 6, wherein said monitoring system, as part of the initiation of an "other-gas detected" condition, illuminates a yellow indicator.

8. The area monitor as recited in claim 6, further comprising an "other-gas data table" as part of a memory circuit, and wherein numeric values of the concentration of the target gas, as determined by the resistance of said first sensor, are stored into said "other-gas data table" during an "other-gas detected" condition.

9. The area monitor as recited in claim 2, wherein said pre-determined time intervals occur as often as one second.

10. The area monitor as recited in claim 2, wherein said first sensor requires calibration as infrequently as once per year.

11. The area monitor as recited in claim 2, wherein said first and second sensors comprise a first zone of detection, and further comprising a second zone of detection which interfaces with said monitoring system, and wherein said second zone of detection includes:

(a) a third sensor that exhibits an electrical resistance that responds to variations in concentration of a pre-determined second target gas within an area of detection, said third sensor's resistance being substantially repeatable at various concentrations of said second target gas, said third sensor's resistance being substantially stable over long periods of time; and (b) a fourth sensor that exhibits an electrical resistance that responds to variations in concentration of said pre-determined second target gas within said area of detection, the resistance of said fourth sensor changing in one direction when in the presence of said second target gas, the resistance of said fourth sensor changing in the opposite direction when in the presence of a gas other than the second target gas that becomes introduced into said area of detection.

12. The area monitor as recited in claim 11, wherein the target gas being detected by said first and second sensors is the same chemical as said second target gas.

13. The area monitor as recited in claim 11, wherein the target gas being detected by said first and second sensors is a different chemical than said second target gas.

14. The area monitor as recited in claim 1, wherein said monitoring system further detects whether the concentration of the target gas as determined by the physical parameter of said first sensor has exceeded a pre-determined alarm setpoint, and, if the physical parameter of said second sensor indicates that said target gas is present in the area of detection, said monitoring system initiates an alarm condition.

15. The area monitor as recited in claim 14, wherein in circumstances where said monitoring system detects whether the concentration of the target gas as determined by the physical parameter of said first sensor has exceeded said pre-determined threshold value, and if the physical parameter of said second sensor indicates that said target gas is not present in the area of detection, said monitoring system initiates an "other-gas detected" condition.

16. The area monitor as recited in claim 1, wherein said pre-determined time intervals occur as often as one second.

17. The area monitor as recited in claim 1, wherein said first sensor requires calibration as infrequently as once per year.

18. The area monitor as recited in claim 1, wherein said first and second sensors comprise a first zone of detection, and further comprising a second zone of detection which interfaces with said monitoring system, and wherein said second zone of detection includes:

(a) a third sensor that exhibits a physical parameter that responds to variations in concentration of a pre-determined second target gas within an area of detection; and (b) a fourth sensor that exhibits a physical parameter that responds to variations in concentration of said pre-determined second target gas within said area of detection, the physical parameter of said fourth sensor changing in one direction when in the presence of said second target gas, the physical parameter of said fourth sensor changing in the opposite direction when in the presence of a gas other than the second target gas that becomes introduced into said area of detection.

19. The area monitor as recited in claim 18, wherein the target gas being detected by said first and second sensors is the same chemical as said second target gas.

20. The area monitor is recited in claim 18, wherein the target gas being detected by said first and second sensors is a different chemical than said second target gas.

* * * * *